United States Patent [19]

Makino et al.

[11] Patent Number: 4,900,416

[45] Date of Patent: Feb. 13, 1990

[54] ELECTROPHORETIC METHOD

[75] Inventors: Yoshihiko Makino; Masashi Ogawa, both of Saitama, Japan

[73] Assignee: Fuji Photo Film Co., Ltd., Kanagawa, Japan

[21] Appl. No.: 243,975

[22] Filed: Sep. 13, 1988

[30] Foreign Application Priority Data

Sep. 14, 1987 [JP] Japan .............................. 62-230592

[51] Int. Cl.$^4$ ............................................ G01N 27/26
[52] U.S. Cl. .............................. 204/182.8; 204/299 R
[58] Field of Search ............ 204/182.8, 299 R, 180.1; 356/344

[56] References Cited

U.S. PATENT DOCUMENTS

| 4,548,869 | 10/1985 | Ogawa et al. | 204/299 R X |
|---|---|---|---|
| 4,579,783 | 4/1986 | Ogawa et al. | 204/299 R X |
| 4,582,868 | 4/1986 | Ogawa et al. | 204/182.8 X |
| 4,600,641 | 7/1986 | Ogawa et al. | 204/299 R X |
| 4,657,656 | 4/1987 | Ogawa | 204/299 R |
| 4,699,705 | 10/1987 | Ogawa et al. | 204/182.8 X |
| 4,722,777 | 2/1988 | Ogawa et al. | 204/299 R |
| 4,737,251 | 4/1988 | Carle et al. | 204/182.8 |
| 4,737,258 | 4/1988 | Ogawa et al. | 204/299 R |
| 4,769,408 | 9/1988 | Ogawa et al. | 204/299 R X |

FOREIGN PATENT DOCUMENTS

| 125763 | 11/1984 | European Pat. Off. | 204/182.8 |
|---|---|---|---|
| 139471 | 5/1985 | European Pat. Off. | 204/182.8 |
| 155833 | 9/1985 | European Pat. Off. | 204/299 R |
| 9212751 | 12/1984 | Japan | 204/182.8 |
| 0243550 | 12/1985 | Japan | 204/299 R |
| 1296258 | 12/1986 | Japan | 204/299 R |
| 03001963 | 1/1988 | Japan | 204/299 R |
| 8402001 | 5/1984 | PCT Int'l Appl. | 204/299 R |

Primary Examiner—John F. Niebling
Assistant Examiner—John S. Starsiak, Jr.
Attorney, Agent, or Firm—Jules E. Goldberg

[57] ABSTRACT

An electrophoretic method comprises the steps of positioning a sample, which contains nucleic acid fragments having different numbers of bases, in an electrophoresis medium composed of an electrophoresis gel medium containing an aqueous poly(meth)acrylamide gel prepared by cross-linking polymerization of a (meth)acrylamide compound and a cross-linking agent in the presence of water and a compound having at least one carbamoyl group as a denaturing agent (or modifier), and applying pulsed electric fields to the electrophoresis medium in two directions, thereby to move the nucleic acid fragments in the presence of molecular sieve effects and to separate the nucleic acid fragments.

9 Claims, No Drawings they are separated in the polyacrylamide gel matrix based on differences in their number of bases, i.e. in their molecular weights. After the electrophoresis has been carried out for a predetermined time, the gel membrane is removed from the supports, covered by a thin polymer film, and subjected to autoradiography or processing in a computed radiography apparatus provided with an imaging plate, thereby to form a visible image of the separation pattern. In the case where the electrophoretic separation is carried out by use of a sample containing nucleic acid fragments labeled with a dye or a fluorescent dye, the separation pattern can be converted into a visible image by use of an apparatus provided with a photoelectric conversion element.

ELECTROPHORETIC METHOD

BACKGROUND OF THE INVENTION

1. Field of the Invention

This invention relates to an electrophoretic method utilizing an electrophoresis medium membrane containing an aqueous poly(meth)acrylamide gel for determination of base sequences of nucleic acids such as a DNA and a RNA.

2. Background of the Invention

With the rapid advances made in research on genetic engineering in recent years, there has arisen a need for quick operations for determination of base sequences of nucleic acids such as a DNA and a RNA.

In the technique for determining base sequences of nucleic acids, slab electrophoresis using an electrophoresis medium membrane containing an aqueous polyacrylamide gel (hereinafter referred to as a polyacrylamide gel membrane or simply as a gel membrane) is indispensable.

The Maxam-Gilvert method according to a chemical degradation process and the dideoxy method according to an enzyme process have heretofore been utilized as the method of preparing a nucleic acid fragment for base sequence reading or determination of a nucleic acid. The dideoxy method enables determination of many base sequences by a single degradation operation, and is therefore popular.

By way of example, the operation of electrophoresis utilizing the polyacrylamide gel membrane as the electrophoresis medium is carried out in the manner as described below.

A polyacrylamide gel membrane having sample slots (i.e. sample spotting holes) at an upper edge is provided between light-permeable, water-impermeable supports, for example, glass plates or organic polymer sheets formed of polyethylene terephthalate or the like, and is disposed vertically. A predetermined amount of a sample (for example, a $^{32}P$-labeled DNA degradated according to the Maxam-Gilvert method) containing nucleic acid fragments having different numbers of bases is spotted into the sample slots, and is subjected to electrophoresis by the application of an electric field. The electrophoresis is carried out by applying a DC voltage, which gives a predetermined electric field per unit length (for example, within the range of 25 V/cm to 70 V/cm) to the polyacrylamide gel membrane, along a predetermined direction (in general, such that the lower side is at higher potential and the upper side is at lower potential). As long as the electric field is applied, DNA molecules (DNA fragments) as high molecular electrolytes having negative charges migrate from the lower-potential side (cathode) to the higher-potential side (anode). As the DNA molecules migrate, they are separated in the polyacrylamide gel matrix based on differences in their number of bases, i.e. in their molecular weights.

With the autoradiography, an X-ray photographic film is closely contacted with the thin film covering the polyacrylamide gel membrane, and exposed to $\beta$-rays from $^{32}P$ or $^{35}S$ at a low temperature (for example, 80° C. below the freezing point) for a predetermined time (for example, within the range of approximately 10 hours to approximately 20 hours). After the exposure, the X-ray photographic film is developed to form a visible image of the electrophoretic separation pattern of the DNA fragments.

The base sequence reading or determination of a DNA can be achieved based on the electrophoretic separation pattern of the DNA fragments obtained in the manner as mentioned above.

However, in the case of the electrophoretic separation pattern of the DNA fragments which is obtained by the conventional method, the band intervals of the separation pattern become markedly wide in the low molecular region wherein the number of bases of the DNA molecule is smaller than approximately $5 \times 10^1$ (the molecular weight is smaller than approximately $1.5 \times 10^4$), and become markedly narrow in the high molecular region wherein the number of bases of the DNA molecule is larger than approximately $2 \times 10^2$ (the molecular weight is larger than approximately $6 \times 10^4$). In the low molecular region, there arises portions where no electrophoretic separation pattern appears in the gel medium membrane. On the other hand, in the high molecular region, it is difficult to determine the base sequence. Therefore, the number of bases for which the base sequence can be determined with a single electrophoresis medium membrane is limited to a small number.

In order to increase the number of base sequences of a DNA readable or determinable by a single operation of electrophoresis, there has heretofore been employed a method wherein the length of the gel membrane is increased to a value within the range of, for example, 80 cm to 100 cm, a method wherein the DNA is labeled with $^{35}S$, instead of $^{32}P$, in order to increase the intensity of $\beta$-rays for the purpose of improving the resolution of the separation pattern, or a method wherein a polyacrylamide gel membrane provided with a gel concentration gradient is employed for the purpose of changing the separation characteristics of the gel membrane. However, even with these improvement methods, large nonuniformity in the band intervals of the separation pattern arises over the range from the low molecular region to the high molecular region of the DNA.

As the technique of controlling the fractionation pattern (band intervals), there has heretofore been known to employ a gel membrane provided with a gel concentration gradient, a membrane provided with a pH buffer concentration gradient, or a membrane provided with a membrane thickness gradient. However, there has not yet been known such a technique that can change the fractionation pattern (band intervals) by controlling the conditions of electrophoresis.

DESCRIPTION OF THE PRIOR ART

In recent years, as a method of separating a big, double-helix DNA (approximately 20 kbp or more), there have been reported electrophoretic methods utilizing a pulse power source, for example, a method as reported in G. F. Carle et al., "Science", 232, 65(1986) wherein the direction of an electric field is inversed by 180° with a period within the range of one second to several hundreds of seconds, and a method as described in Charles R. Cantor et al., "Cell", 37, 67(1984) or Japanese Patent Publn. No.59(1984)-502037 (WO84/02001) wherein electric fields are applied from two intersecting directions. These techniques are for the separation of a big, double-helix DNA on the order of $10^4$ bp to $10^5$ bp (a molecular weight within the range of $6 \times 10^6$ to $6 \times 10^7$), said separation being effected on the order of $10^3$ bp based on a difference in the number of bases (a difference in the molecular weight). These techniques are markedly different from the electrophoretic method used for the base sequence reading or determination of a DNA wherein a small, single-chain DNA (molecular weight to be separated for the base sequence reading or determination of the DNA) having the number of bases within the range of $10^1$ b to $10^3$ b (a molecular weight within the range of $3 \times 10^3$ to $3 \times 10^6$) is separated up to a difference of the unit of a single base. At any rate, there has not heretofore been known any technique of improving the separation pattern for the base sequence reading or determination of a DNA based on an improvement of the electrophoretic method.

SUMMARY OF THE INVENTION

The primary object of the present invention is to provide an improved electrophoretic method for base sequence reading or determination of a DNA, which eliminates nonuniformity in band intervals (fractionation pattern) in electrophoresis for base sequence reading or determination of a DNA.

Another object of the present invention is to provide an improved electrophoretic method for base sequence reading or determination of a DNA, which makes band widths uniform and enables determination of markedly a larger number of base sequence than with the conventional method by a single electrophoretic separation pattern.

The present invention provides an electrophoretic method comprising the steps of:

(i) positioning a sample, which contains nucleic acid fragments having different numbers of bases, in an electrophoresis medium composed of an electrophoresis gel medium containing an aqueous poly(meth)acrylamide gel prepared by cross-linking polymerization of a (meth)acrylamide compound and a cross-linking agent in the presence of water and a compound having at least one carbamoyl group as a denaturing agent (or modifier), and (ii) applying pulsed electric fields to said electrophoresis medium in two directions, thereby to move said nucleic acid fragments in the presence of molecular sieve effects and to separate said nucleic acid fragments.

With the electrophoretic method in accordance with the present invention, band intervals of a separation pattern of DNA fragments can be changed readily by the selection of the conditions of the pulsed electric fields, and therefore the electrophoretic method can readily be applied to electrophoresis for the reading or determination of various DNA base sequences.

With the electrophoretic method in accordance with the present invention, also for a single-chain DNA having the number of bases on the order of $10^2$, the band intervals of DNA fragments in an objective region of the number of bases can be widened or narrowed by the selection of the conditions of the pulsed electric fields.

The conventional technique has the problem that the band intervals are very narrow in the region of the number of bases on the order of several hundreds, and an error is readily caused in the base sequence reading of a DNA. However, with the electrophoretic method in accordance with the present invention, the band intervals of a separation pattern of DNA fragments can be widened readily by the selection of the conditions of the pulsed electric fields, and therefore the aforesaid problem can be eliminated.

Also, with the electrophoretic method in accordance with the present invention, the band intervals of a separation pattern of DNA fragments can be narrowed in the low molecular region and can be widened in the high molecular region by the selection of the conditions of the pulsed electric fields. Therefore, bases in a number larger than with the conventional technique can be read by use of a single polyacrylamide gel medium having the same migration distance as in the conventional technique.

DETAILED DESCRIPTION OF THE INVENTION

In this specification, acrylamide as a monomer and its derivatives are referred to as the acrylamide compound, and methacrylamide and its derivatives are referred to as the methacrylamide compound. The acrylamide compound and the methacrylamide compound are generically referred to as the (meth)acrylamide compound. Also, explanations common to the acrylamide compound and the methacrylamide compound will often be made for the acrylamide compound. The term "aqueous poly(meth)acrylamide gel" as used herein means an aqueous polyacrylamide gel, an aqueous polymethacrylamide gel, and an aqueous acrylamide-methacrylamide copolymer gel. Explanations common to these gels will often be made for the aqueous polyacrylamide gel.

The electrophoresis medium used in the electrophoretic method in accordance with the present invention may be in an ordinarily used form, for example, a thin layer-shaped form, a thin plate-shaped form, a thin membrane-shaped form (these three forms are generically referred to as a membrane), a columnar or rod-shaped form, or a prism-shaped form. In general, the membrane-shaped electrophoresis medium, i.e. the electrophoresis medium membrane, is preferable used.

The electrophoresis medium used in the electrophoretic method in accordance with the present invention may be a gel membrane having a constant gel concentration and a constant membrane thickness, or a gradient membrane, for example, a membrane thickness gradient membrane, a gel concentration gradient membrane, a buffer concentration gradient membrane or a gel concentration gradient - membrane thickness gradient membrane. The gel concentration of the gel medium may be within an ordinarily applicable range, and may be within the range of, for example, 4% w/v to 25% w/v. The membrane thickness may be within an ordinarily applicable range, and may be within the range of, for example, 100 μm to 500 μm for facilitating the operation.

The electrophoresis medium used in the electrophoretic method in accordance with the present invention is composed of the electrophoresis gel medium containing the aqueous poly(meth)acrylamide gel prepared by cross-linking polymerization of the (meth)acrylamide compound as a monomer and a cross-linking agent in the presence of water and a compound such as urea having at least one carbamoyl group as a denaturing agent (or modifier). The composition of the gel medium and the method of forming the gel may be selected from those described in, for example, "Saishin Denkieidoho" (Up-to-date Electrophoresis) by Aoki and Nagai, Hirokawa Shoten, pp. 370–415 (1978); "Electrophoresis,"]2, 213–219; "Electrophoresis," 2, 220–228; Japanese Unexamined Patent Publication Nos. 59(1984)-126236, 60(1985)-60548, 60(1985)-235819, 61(1986)-2058, 61(1986)-18852, 61(1986)-28512, 62(1987)-91849; and 63(1988)-70156.

By way of example, the composition of the gel medium may be an aqueous solution (solution for gel formation) containing acrylamide (monomer), a cross-linking agent (such as N',N'-methylenebisacrylamide or 1,3,5-triacryloylhexahydro-s-triazine), a polymerization initiator composition, a pH buffer agent, and optionally a water-soluble polymer (such as agarose, poly(vinylpyrrolidone), polyacrylamide). The aqueous solution is subjected to cross-linking polymerization in an elongated cylinder, in an elongated prism, in a thin space between two glass plates, in a vessel or on an organic polymer sheet (support) in an atmosphere free of oxygen, thereby to form the aqueous gel medium. In the case where a long aqueous gel medium is to be formed continuously from the solution for gel formation, the aqueous gel medium may preferably be formed on a long sheet of polyethylene terephthalate in an atmosphere free of oxygen in accordance with the method disclosed in Japanese Unexamined Patent Publication No. 59(1984)-126236 or 62(1987)-91849.

In the electrophoretic method of the present invention, the steps of, for example, application (e.g. spotting, injection) of the sample containing nucleic acid fragments having different numbers of bases to the gel medium prior to the application of the electric fields in two directions may be carried out in the same manner as in the conventional procedure. For example, one of the preferable methods is to apply the sample to the sample spotting holes of the gel medium membrane, and to apply a DC electric field for a time within the range of approximately five minutes to approximately ten minutes in the ordinary direction of migration until the sample has moved by a short distance in the desired direction of migration and is positioned at a predetermined migration start point inside of the gel medium membrane. Thereafter, a pulsed electric field is applied to the gel medium on which the sample has been applied. The pulsed electric field is inverted by 180° (i.e. reversed) with a predetermined period. Pulsed electric fields are not simultaneously applied in opposite directions. The strength of the electric field is within the same range as the strength of the DC electric field applied in accordance with the conventional procedure. The waveform of the pulsed electric field may be of any type such as a square wave, a saw tooth wave, triangular wave or a sine wave.

In the case where the strength of the electric field in the direction that causes the DNA fragment to advance is denoted by EF, the strength of the electric field in the direction that causes the DNA fragment to return is denoted by ER, the time of duration of a single electric field pulse in the direction that causes the DNA fragment to advance is denoted by TF, and the time of duration of a single electric field pulse in the direction that causes the DNA fragment to return is denoted by TR, the conditions of application of the inverted pulsed electric field may be such that, for example, EF and ER are respectively within the range of approximately 10 V/cm to approximately 150 V/cm, preferably within the range of approximately 20 V/cm to approximately 100 V/cm, and EF=ER, EF>ER, or EF<ER; and TF and TR are respectively within the range of approximately 0.1 msec to approximately 100 msec, preferably within the range of approximately 1 msec to approximately 50 msec, and TF=TR, TF>TR, or TF<TR. Also, the ratio of TF:TR may be within the range between approximately 5:1 and approximately 2:1, and should preferably be approximately 3:1. However, EF, ER, TF and TR should be combined with one another so that the DNA fragment can advance. In general, the combinations are such that EF=ER and TF>TR; EF>ER and TF=TR; and EF>ER and TF>TR, among which the conditions of EF=ER, TF>TR and the TF:TR ratio being approximately 3:1 are preferable.

Electrophoresis is carried out for a time required for the separation of the number of bases necessary for the base sequence reading or determination of a DNA, and the electrophoresis time is not limited to a particular time. For example, a marker dye such as Xylene Cyanol may be poured to a single lane of the gel medium, the distance of migration of the marker dye may be read, and the application of the electric field may be stopped at the time a predetermined distance of migration is reached.

The range of the numbers of bases for which the base sequences can be read can be increased by carrying out the electrophoretic separation by the application of the pulsed electric field inverted with a predetermined period, and controlling to widen the band intervals in the region of the number of bases within the range of $2 \times 10^2$ to $3 \times 10^2$, wherein the reading of the base sequences is difficult with the conventional electrophoretic separation using an electric field in a single direction (DC electric field), while the number of bases at the lowest edge of a single separation pattern is maintained the same.

Processing for converting the separation pattern appearing after the operation of electrophoretic separation is finished into a visible image may be carried out in accordance with the conventional procedure.

The present invention will further be illustrated by the following nonlimitative examples.

EXAMPLE 1 AND COMPARATIVE EXAMPLE 1

A gel vessel was made by providing two transparent glass plates having smooth surfaces as supports to face each other with a space of 200 μm intervening therebetween in accordance with the conventional procedure. An aqueous polyacrylamide gel membrane (concentration: 8.0% w/v) was prepared in the vessel and used as an electrophoresis medium membrane.

The gel membrane provided between the two glass plates was vertically positioned in an electrophoretic apparatus provided with electrode liquid vessels at upper and lower end portions (a cathode at the upper end portion and an anode at the lower end portion). The electrode liquid vessels at the upper and lower end portions of the electrophoretic apparatus were filled with a TBE buffer, i.e. a tris(hydroxymethyl)aminomethane - disodium ethylenediaminetetraacetate - boric acid buffer (pH 8.3), as an electrode liquid. A DNA fragment sample prepared by use of M-13mp8 DNA in accordance with the dideoxy method was spotted into sample slots at the upper edge of the gel medium membrane by use of a micro-syringe in an amount of 1 μl per sample slot.

[Operation of Electrophoresis]

(1) Method in Accordance With the Present Invention

After the DNA sample was poured, a DC electric field at 35 V/cm (the lower edge side at a higher potential) was applied to the gel medium membrane for approximately 10 minutes, thereby to move the DNA sample to the migration start position inside of the gel membrane. Thereafter, electrophoretic separation was carried out until a marker dye (Xylene Cyanol FF; Color Index No42135; CA Registry No[2650-17-1]) has moved by 27 cm by applying an electric field nearly corresponding to a square wave in accordance with two switching cycles shown in Table 1 below.

(2) Conventional Technique

After the DNA sample was poured, electrophoretic separation was carried out until a marker dye (Xylene Cyanol FF) has moved by 27 cm by applying a DC electric field at 35 V/cm on the average (the lower edge side at a higher potential) to the gel medium membrane.

[Conversion of Separation Pattern into Visible Image]

The gel medium membrane on which the operation of electrophoresis has been finished was subjected to autoradiography in accordance with the conventional procedure for converting the electrophoretic separation pattern of the DNA fragment sample into a visible image on an X-ray photographic film.

[Evaluation of Electrophoretic Method]

Band intervals and the number of readable bases were investigated for the visible image of the electrophoretic separation pattern of the DNA fragment sample on the X-ray photographic film, and results shown in Table 1 were obtained.

TABLE 1

|  |  | Example 1 | | Comp. Ex. 1 |
| --- | --- | --- | --- | --- |
|  |  | A | B |  |
| Electric field conditions | EF | 35 V/cm | — | — |
|  | Pulse duration time | 15 msec | 90 msec | Continuous |
|  | ER | 35 V/cm | — | None |
|  | Pulse duration time | 5 msec | 30 msec | None |
| Number of readable bases |  | 240 | 205 | 180 |

—: Indicates the same value as in the left column.
EF: Lower edge side at a higher potential.
ER: Upper edge side at a higher potential.

With the electrophoretic method in accordance with the present invention wherein the pulsed electric field was inverted by 180² and thus was applied periodically in two directions, the band in the top edge region of the electrophoretic separation pattern of the DNA fragment sample was shifted toward the upper side of the gel membrane, and consequently the band intervals were widened in the high molecular region. The results shown in Table 1 revealed that, with the electrophoretic method in accordance with the present invention, the number of readable bases is increased by approximately 33% in A of Example 1 and by approximately 13% in B of Example 1 as compared with the conventional technique wherein a DC electric field is applied.

EXAMPLE 2 AND COMPARATIVE EXAMPLE 2

The same procedures as in Example 1 and Comparative Example 1 were carried out by use of a prefabricated polyacrylamide gel membrane (supplied by Fuji Photo Film Co., Ltd., gel concentration of 8.0% w/v, membrane thickness of 0.2 mm, 40 cm long×20 cm wide) provided between two polyethylene terephthalate films (transparent supports). In this manner, results shown in Table 2 below were obtained.

With the electrophoretic method in accordance with the present invention wherein the pulsed electric field was inverted by 180° and thus was applied periodically in two directions, the band in the top edge region of the electrophoretic separation pattern of the DNA fragment sample was shifted toward the upper side of the gel membrane, and consequently the band intervals were widened in the high molecular region. The results shown in Table 2 revealed that, with the electrophoretic method in accordance with the present invention, the number of readable bases is increased by approximately 28% as compared with the conventional technique wherein a DC electric field is applied.

TABLE 2

|  |  | Example 2 | Comp. Ex. 2 |
| --- | --- | --- | --- |
| Electric field conditions | EF | 35 V/cm | 35 V/cm |
|  | Pulse duration time | 15 msec | Continuous |
|  | ER | 35 V/cm | None |
|  | Pulse duration time | 5 msec | None |
| Number of readable bases |  | 230 | 180 |

EF: Lower edge side at a higher potential.
ER: Upper edge side at a higher potential.

We claim:

1. An electrophoretic method comprising the steps of:
   (i) positioning a sample, which contains nucleic acid fragments having different numbers of bases, in an electrophoresis medium composed of an electrophoresis gel medium containing an aqueous poly(meth)acrylamide gel prepared by the cross-linking polymerization of a (meth)acrylamide compound and a cross-linking agent in the presence of water and a compound having at least one carbamoyl group as a denaturing agent, and
   (ii) applying pulsed electric fields to said electrophoresis medium in two directions, the electric field strength in each direction being from about 10 V/cm to 150 V/cm, and the duration of each pulse being from about 0.1 msec to 100 msec, to move thereby said nucleic acid fragments in the presence of a molecular sieve effect and to separate said nucleic acid fragments.

2. A method as defined in claim 1 wherein said pulsed electric fields in two directions are opposite to each other and do not substantially intersect each other.

3. A method as defined in claim 1 wherein said pulsed electric fields in two directions are alternately applied with a predetermined period.

4. A method as defined in claim 3 wherein the pulsed electric field applied in the direction that causes said nucleic acid fragments to move forward is applied for a relatively longer duration time.

5. A method as defined in claim 1 wherein said pulsed electric fields in two directions are alternately applied with substantially equal strengths.

6. A method as defined in claim 1 wherein said electrophoresis medium is a thin plate-shaped or thin membrane-shaped electrophoresis medium membrane having a substantially constant gel concentration and a substantially constant thickness.

7. A method as defined in claim 1 wherein said electrophoresis medium is a thin plate-shaped or thin membrane-shaped electrophoresis medium membrane provided with at least one gradient selected from the group consisting of a membrane thickness gradient, a gel concentration gradient and a pH buffer concentration gradient.

8. A method as defined in any of claims 1 to 7 wherein said electrophoresis medium is provided on a sheet-shaped support formed of an organic polymer.

9. A method as defined in any of claims 1 to 7 wherein said electrophoresis medium is provided on a sheet-shaped support formed of glass.

* * * * *